United States Patent
Hashimoto et al.

(10) Patent No.: US 8,524,212 B2
(45) Date of Patent: Sep. 3, 2013

(54) PROPHYLACTIC AND/OR THERAPEUTIC DRUG FOR NONALCOHOLIC STEATOHEPATITIS

(75) Inventors: Etsuko Hashimoto, Tokyo (JP); Makiko Taniai, Asaka (JP); Keiko Shiratori, Tokyo (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 934 days.

(21) Appl. No.: 12/107,380

(22) Filed: Apr. 22, 2008

(65) Prior Publication Data

US 2009/0110655 A1 Apr. 30, 2009

(30) Foreign Application Priority Data

Oct. 24, 2007 (JP) ................. 2007/276510

(51) Int. Cl.
*A61K 31/787* (2006.01)
*A61P 1/16* (2006.01)

(52) U.S. Cl.
USPC ...................... 424/78.1; 242/78.08

(58) Field of Classification Search
USPC ............. 424/78.1, 78.08
See application file for complete search history.

(56) References Cited

U.S. PATENT DOCUMENTS

| 4,777,042 A | 10/1988 | Toda et al. |
| 6,562,329 B2 * | 5/2003 | Hadvary et al. ........... 424/78.08 |
| 2004/0067215 A1 | 4/2004 | Suzuki et al. |
| 2004/0191209 A1 | 9/2004 | Oba |
| 2007/0212325 A1 * | 9/2007 | Suzuki et al. ............ 424/78.12 |
| 2008/0194575 A1 * | 8/2008 | Beraza et al. ........... 514/252.14 |

FOREIGN PATENT DOCUMENTS

| JP | 60-209523 | 10/1985 |
| WO | 02/09757 | 2/2002 |
| WO | WO 02/43761 A1 | 6/2002 |
| WO | WO 03/011308 A1 | 2/2003 |
| WO | WO 2005/092349 A1 | 10/2005 |

OTHER PUBLICATIONS

Mark H. Beers and Robert Berkow (Editors), The Merck Manual of Diagnosis and Therapy, Seventeenth Edition, p. 367.*
The Merk Manual of Diagnosis and Therapy. Seventeenth Edition pp. 366 and 367 (1999).*
Gastrenterology: AGA Technical Review on Nonalcoholic Fatty Liver Disease. vol. 123 pp. 1705-1724 (2002).*
The Merk Manual of Home Health Handbook. Test for Liver, Gallblader, and Biliary Disorders Online Edition (2011).*
A.D.A.M. Medical Encyclopedia. Metabolic Syndrome. Online Edition. 2011.*
Kengo Tomita, et al., "Management and Treatment of Nonalcoholic Steatohepatitis: Promising Pharmacological Therapies" Prog Med. 2005, vol. 25, No. 6, 1629-1636 w/English Translation.
Hiroshi Shuto, "Treatment of fatty liver occurring in association with lipid dysbolism" Modern Physician vol. 27, No. 8, 2007-8, P. 1161 (English translation only).
Kengo Tomita, et al., "Management and Treatment of Nonalcoholic Steatohepatitis: Promising Pharmacological Therapies" Prog Med. 2005, vol. 25, No. 6, 1629-1636 w/English Abstract.

* cited by examiner

*Primary Examiner* — Anoop Singh
*Assistant Examiner* — Anna Falkowitz
(74) *Attorney, Agent, or Firm* — Oblon, Spivak, McClelland, Maier & Neustadt, L.L.P.

(57) ABSTRACT

The present invention provides a method for the treatment of nonalcoholic steatohepatitis with a pharmaceutically acceptable anion exchange resin such as, for example, colestimide.

9 Claims, 2 Drawing Sheets

PROPHYLACTIC AND/OR THERAPEUTIC DRUG FOR NONALCOHOLIC STEATOHEPATITIS

FIELD OF THE INVENTION

The present invention relates to treating nonalcoholic steatohepatitis.

BACKGROUND OF THE INVENTION

Nonalcoholic fatty liver disease (NAFLD) includes simple steatosis free of hepatic fibrosis and infiltration of inflammatory cells, and nonalcoholic steatohepatitis (NASH) accompanied by hepatic fibrosis and infiltration of inflammatory cells.

As the onset mechanism of NASH, a two-hit theory is widely supported, wherein triglyceride deposition (fatty liver) occurs in hepatocytes (first hit), and a cause of hepatocellular injury (second hit) thereon triggers the onset. It is assumed that the first hit is caused by the uptake, synthesis and catabolism of fatty acid and triglyceride release by hepatocytes, and the second hit is caused by oxidation stress, endotoxin, adipocytokine and the like (non-patent reference 1).

At the time of diagnosis, cirrhosis occurs in association with 2-28% of NASH a complication and, even in the case of NASH not in association with cirrhosis as a complication, about 20% is considered to progress to cirrhosis in about 10 years. The diagnostic and therapeutic methods of chronic hepatitis B and chronic hepatitis C, which are important causes of cirrhosis and liver cancer, are being established in recent years. In contrast, as for NAFLD and NASH, which are the other important causes of cirrhosis and liver cancer, elucidation of their pathology has just begun, and establishment of diagnostic methods and therapeutic methods is urgently needed. In non-patent reference 2, the onset and progress mechanism of NASH is considered using a hepatocyte specific Pten knockout mouse.

NAFLD often accompanies complications such as obesity, diabetes, hyperlipidemia, hypertension and the like, and is considered a metabolic syndrome. In NASH, a drug therapy of obesity, diabetes, hyperlipidemia, hypertension and the like behind NASH is important (non-patent reference 3).

Of the diabetic drugs, however, an •-glucosidase inhibitor, a sulfonylurea agent, a fast-acting insulin secretagogue and the like have not been reported as prophylactic and/or therapeutic drugs for NASH. Of the therapeutic drugs for hyperlipidemia, moreover, nicotinic acid derivatives have not been reported as prophylactic and/or therapeutic drugs for NASH. Therefore, it is presumed that not all therapeutic drugs for obesity, diabetes, hyperlipidemia, hypertension and the like are effective for NASH.

Colestimide is known to act as a hypocholesterolemic agent, an antiobesitic agent, a postprandial hyperglycemia improving agent or an insulin sensitizer (patent references 1-4). However, it is not known whether colestimide is effective for the prophylaxis or treatment of NASH.

[patent reference 1] JP-A-60-209523
[patent reference 2] WO02/43761
[patent reference 3] WO03/011308
[patent reference 4] WO2005/092349
[non-patent reference 1] Medical Care Guide of NASH•NAFLD (ed. the Japan Society of Hepatology) BUNKODO CO., LTD (Bunkodo) p 14-23 published on Aug. 22, 2006
[non-patent reference 2] Liver, vol. 45, No. 11, 568-580 (2004)
[non-patent reference 3] Medical Care Guide of NASH•NAFLD (ed. the Japan Society of Hepatology), BUNKODO CO., LTD. p 40-42, published on Aug. 22, 2006

SUMMARY OF THE INVENTION

The present invention aims at providing a novel prophylactic and/or therapeutic drug for NASH (hereinafter to be also simply referred to as "pharmaceutical agent").

The present inventors have conducted intensive studies in an attempt to solve the aforementioned problems and found that an anion exchange resin represented by colestimide acts on NASH safely and effectively, which resulted in the completion of the present invention.

According to the present invention, a safe and effective prophylactic and/or therapeutic drug for NASH can be provided, and a further treatment effect is expected by the use of the drug as a pharmaceutical agent for an administration regimen in combination with, in particular, a lifestyle guidance.

Accordingly, the present invention provides the following.
[1] A prophylactic and/or therapeutic drug for the treatment of nonalcoholic steatohepatitis in a patient by administering a pharmaceutically acceptable anion exchange resin as an active ingredient.
[2] The pharmaceutically acceptable anion exchange resin is in one embodiment capable of adsorbing bile acid.
[3] In another embodiment, the pharmaceutically acceptable anion exchange resin is selected from colestimide, cholestyramine resin, colestipol, sevelamer and colesevelam.
[4] In another embodiment, the pharmaceutically acceptable anion exchange resin is synthesized by polymerizing an epichlorohydrin derivative and an amine.
[5] In another embodiment, the pharmaceutically acceptable anion exchange resin is colestimide.

DETAILED DESCRIPTION OF THE INVENTION

Figure 1:
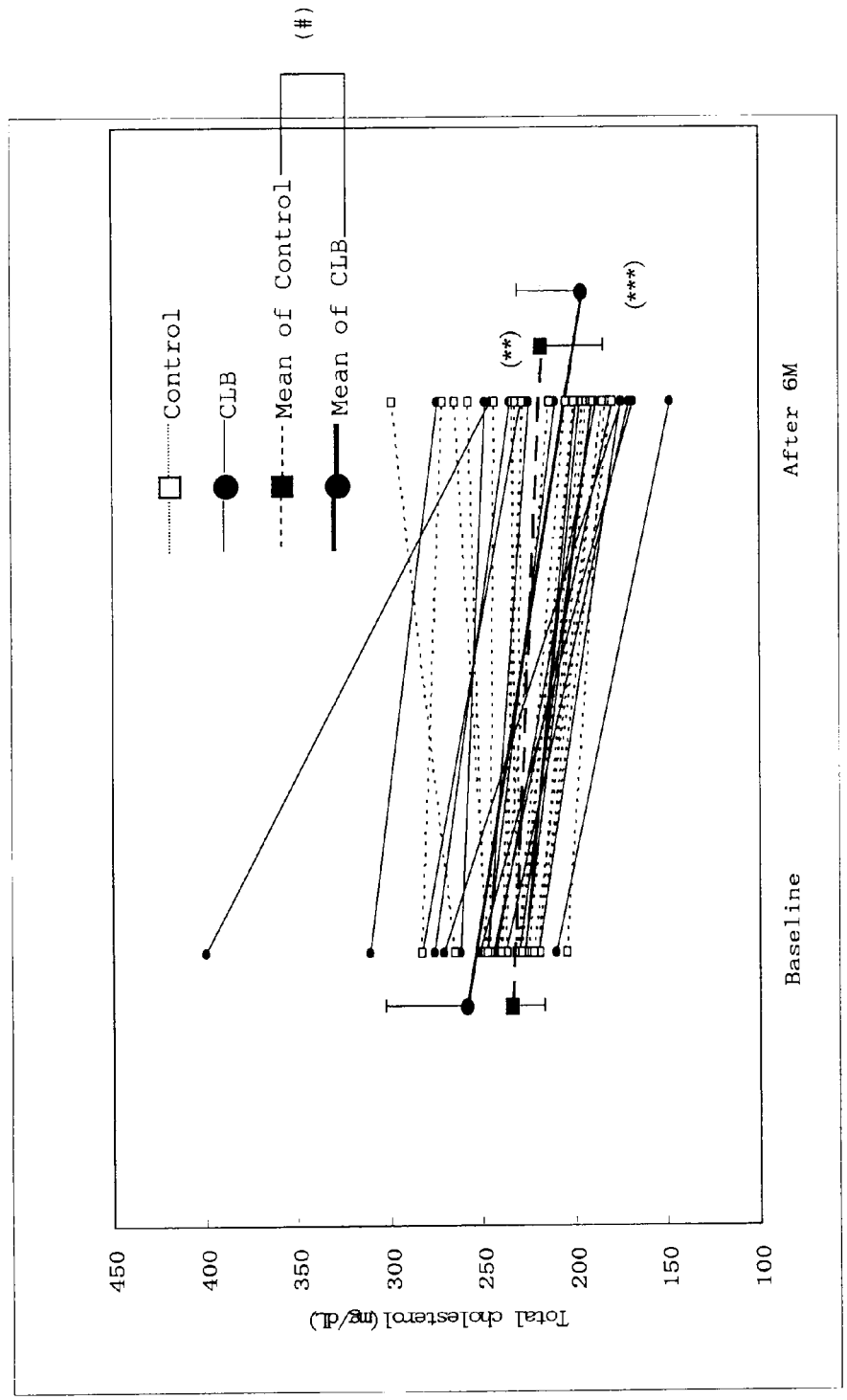
FIG. 1 The figure shows changes in the total cholesterol values between before and after the test in the control group and the colestimide administration group.

According to the "Medical Care Guide of NASH•NAFLD (ed. the Japan Society of Hepatology)", a case of steatohepatitis accompanied by necrosis, inflammation or fibrosis in hepatic tissues but free of clear drinking history in the clinical history is referred to as NASH (no characteristic conscious disorder, many cases with high levels of ALT, AST as compared to simple steatosis in liver function tests, 5-20% of the cases develops cirrhosis in 5-10 years). The progression of hepatic diseases is determined by classifying each of the activity levels of inflammation and necrosis (grading of activity) and progression of fibrosis (staging of fibrosis). Inflammation and necrosis are divided into 4 levels of A0-A3 sequentially from an inflammation-free, necrosis-free condition, and fibrosis is divided into 5 levels of F0-F4 sequentially from a fibrosis-free condition. F0-F3 correspond to hepatitis and F4 corresponds to cirrhosis.

In the present invention, the pharmaceutically acceptable anion exchange resin is an anion exchange resin that can be administered as a pharmaceutical product, and preferred is an anion exchange resin capable of adsorbing bile acid.

One example thereof is most preferably colestimide(2-methylimidazole-epichlorohydrin copolymer). While colestimide has an irregularly assembled and complicated stereostructure, it is shown by the fundamental structure of the following formula (I), which is partially shown by the following formula (II), and can be obtained by a polymerization reaction of an epichlorohydrin derivative (or compound) and an amine represented by imidazole derivatives, i.e., the production method described in JP-A-60-209523.

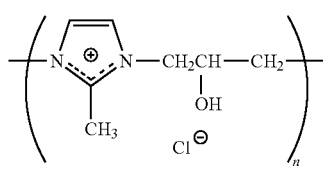
(I)

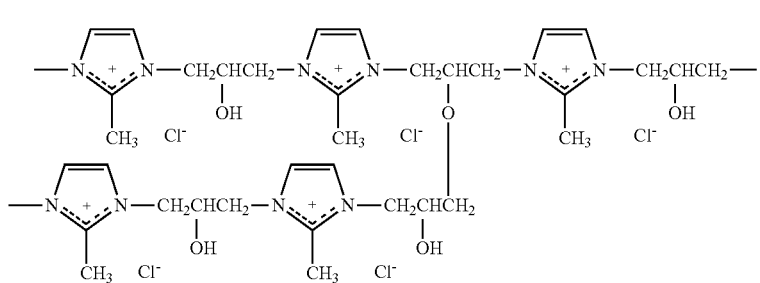
(II)

Colestimide is registered in JAN with a general name colestimide (chemical name: 2-methylimidazole-epichlorohydrin copolymer), and in INN, it is registered with a general name colestilan (chemical name: 2-methylimidazole polymer with 1-chloro-2,3-epoxypropane).

Other preferable anion exchange resin includes the aforementioned cholestyramine resin, colestipol (N-(2-aminoethyl)-N'-[2-[(2-amino-ethyl)amino]ethyl]-1,2-ethanediaminepolymer added with (chloromethyl)oxirane) and the like, which are commercially available from Sigma Ltd. The cholestyramine resin is a strongly basic anion exchange resin including a styrene-divinylbenzene copolymer added with a quaternary ammonium group, whose fundamental structure is represented by the following formula (III):

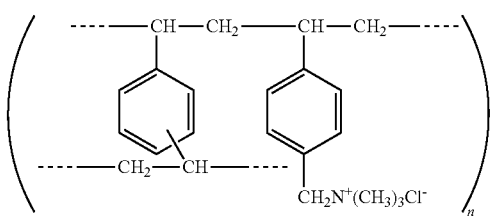
(III)

In addition, the fundamental structure of sevelamer is represented by the following formula and can be produced by the method described in U.S. Pat. No. 5,496,545 or a method analogous thereto. The salt is not limited to a hydrochloride.

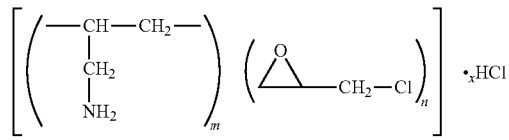

The fundamental structure of colesevelam is represented by the following formula and can be produced by the method described in U.S. Pat. No. 5,607,669 or a method analogous thereto. The salt is not limited to a hydrochloride and may be a carbonate.

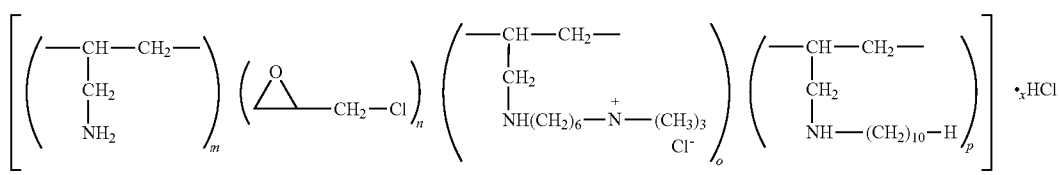

In addition, other anion exchange resins described in JP-A-9-504782, 9-500368, 10-501264, 10-501842, 11-507093, 11-512074 and 5-512332, as well as JP-A-8-208750, 9-202732, 10-114661 and 11-228449 and the like can be used in the present invention as long as they do not go beyond the gist of the present invention.

Examples of the epichlorohydrin derivative include, besides epichlorohydrin, 2-methylepichlorohydrin, 2-ethylepichlorohydrin and the like.

Examples of the amine include amines represented by imidazole derivatives.

As the pharmaceutical agent of the present invention, the aforementioned compounds, which are active ingredients, may be used as they are, or a pharmaceutical composition containing the aforementioned active ingredient may be more preferably produced using general additives for preparations and put to use.

Examples of such pharmaceutical composition include tablet, capsule, fine granules, pill, troche, liquid and the like, which are administered orally (including sublingual administration).

The pharmaceutical agent of the present invention can be produced by a conventional method widely used such as mixing, filling, compressing and the like. Moreover, by applying repeated formulation procedures, colestimide, an active ingredient, may be distributed in a pharmaceutical agent containing a large amount of excipient.

For example, when the pharmaceutical agent of the present invention is a solid, a tablet or capsule used for oral administration is preferably provided as a unit dosage form, and may contain a generally-used carrier for preparations such as binder, excipient, diluent, compressing agent, lubricant, disintegrant, colorant, flavor, moistening agent and the like. Tablets may be provided as coated tablets using a coating agent according to a method well known in the art.

Examples of preferable excipient include cellulose, mannitol, lactose and the like.

Examples of preferable disintegrant include starch, polyvinylpyrrolidone, starch derivative such as sodium starch glycolate and the like, and the like.

Examples of preferable lubricant include sodium lauryl sulfate and the like.

Oral pharmaceutical compositions in the form of a liquid are provided, for example, as pharmaceutical compositions such as aqueous or oily suspension, solution, emulsion, syrup, elixir and the like, or as dry pharmaceutical compositions that can be re-dissolved before use in water or a suitable medium.

When the pharmaceutical agent of the present invention is a liquid, additives generally used for liquids can be used. Examples of additive include precipitation preventing agent, emulsifier, oily ester, non-aqueous medium, preservative, flavor, colorant and the like.

Examples of preferable precipitation preventing agent include sorbitol, syrup, methylcellulose, gelatin, hydroxyethylcellulose, carboxymethylcellulose, aluminum stearate gel, hydrogenated edible fat and the like.

Examples of preferable emulsifier include lecithin, sorbitan monooleate, gum arabic and the like.

Examples of preferable oily ester include almond oil, refined coconut oil, glycerin ester and the like.

Examples of preferable non-aqueous medium include propylene glycol, ethyl alcohol and the like.

Examples of preferable preservative include methyl ester, ethyl ester or propyl ester of p-hydroxybenzoic acid, sorbic acid and the like.

The active ingredient of the pharmaceutical agent of the present invention is contained in a proportion of generally 5-95 wt %, preferably 25-90 wt %, more preferably 75-85 wt %, when it is a solid agent. When it is a liquid, the active ingredient is contained in a proportion similar to that in the solid agent as long as the effect of the invention is afforded.

Colestimide is commercially available from Mitsubishi Tanabe Pharma Corporation in the trade name of CHOLEBINE (registered trade mark), and CHOLEBINE may be directly used in the present invention even when a pharmaceutical composition containing an active ingredient is to be administered.

The dose of the pharmaceutical agent of the present invention can be appropriately determined depending on the age, condition of health and body weight of patients, severity of disease, the kind and frequency of the treatment to be simultaneously performed, the nature of the desired effect and the like. Taking colestimide per day for an adult as an example, the dose is generally 1-10 g, preferably 1.5-6 g, more preferably 3-4.5 g, which is administered in 1 to several portions a day.

When the pharmaceutical agent of the present invention is used as a prophylactic drug, moreover, 1-10 g, preferably 1.5-6 g, more preferably 3-4.5 g, based on colestimide, is generally administered to an adult hyperlipidemia or obesity patients with fatty liver per day in one to several portions a day.

EXAMPLES

The present invention is specifically explained in the following by referring to Examples, which are not to be construed as limitative. The colestimide used below was either commercially available CHOLEBINE (registered trade mark, 500 mg tablet) or CHOLEBINE (registered trade mark) Mini 83% manufactured by Mitsubishi Tanabe Pharma Corporation.

Example 1

Effect of Colestimide on NASH Patients (1) Subjects

The test subjects were NASH patients diagnosed clinicopathologically from March 2005 to May 2006, who developed hyperlipidemia or obesity of not less than BMI 25 as a complication, and signed a written informed consent. The aforementioned patients were randomly divided into a control group (only lifestyle guidance) or a colestimide administration group (lifestyle guidance and colestimide administration) by an envelope method.

(2) Method

The colestimide administration group was administered with colestimide (1,500 mg) two times in total before breakfast and before dinner, and instructions of dietary and exercise therapy were given to the both groups by a national registered dietitian.

The control group: 21 patients (13 males, 8 females), and the colestimide administration group: 17 patients (11 males, 6 females) were the test subjects, and comparison was made between before the test and 6 months from the start of the test.

(3) Patient Back Ground

By comparison of the backgrounds of the control group and the colestimide administration group, the ratio of the female was 38%:35%, the age median value (minimum value-maximum value) was 46 years old (31-85):46 years old (27-77), the BMI median value was 25.4 (21.3-37.3):24.8 (21.8-31.7), the liver biopsy was F1 62%, F3 5%:F1 59%, F3 6%, the visceral fat area was 182 cm$^2$ (109-373):173 cm$^2$ (105-300), and the hepatosplenic CT value ratio was 0.85 (0.43-1.1):0.80 (0.46-1.2), showing no difference, and the both groups did not show difference in the development of hyperlipidemia as a complication.

(4) Results

The test results of the both groups are shown in Table 1. In the table, BW shows body weight, T-C shows total cholesterol, TG shows triglyceride, BS shows blood glucose, IRI shows insulin, HOMA shows insulin resistance, AST shows aspartic acid aminotransferase, and ALT shows alanine aminotransferase.

TABLE 1

| | Baseline | After 6 months | N | p | p | Before and after administration test |
|---|---|---|---|---|---|---|
| Control | | | | | | |
| BW (kg) | 70.43 ± 13.16 | 68.33 ± 12.08 | 21 | 0.005 | ** | t |
| T-C (mg/dL) | 234.10 ± 17.41 | 217.81 ± 33.48 | 21 | 0.001 | ** | t |
| TG (mg/dL) | 210.90 ± 117.58 | 171.43 ± 99.55 | 21 | 0.001 | ** | t |
| BS (mg/dL) | 105.43 ± 15.18 | 104.86 ± 15.52 | 21 | 0.859 | NS | t |
| IRI (μU/ml) | 15.70 ± 16.72 | 18.66 ± 22.83 | 21 | 0.355 | NS | t |
| HOMA | 4.48 ± 6.03 | 4.87 ± 5.97 | 21 | 0.560 | NS | t |
| AST (IU/37° C.) | 43.90 ± 19.26 | 37.10 ± 16.99 | 21 | 0.035 | * | t |
| ALT (IU/37° C.) | 73.62 ± 48.47 | 61.19 ± 42.59 | 21 | 0.058 | NS | t |
| Colestimide | | | | | | |
| BW (kg) | 70.24 ± 13.22 | 68.12 ± 11.32 | 17 | 0.008 | ** | t |
| T-C (mg/dL) | 258.18 ± 44.47 | 202.71 ± 34.58 | 17 | 0.000 | *** | t |
| TG (mg/dL) | 263.88 ± 345.75 | 159.88 ± 100.91 | 17 | 0.114 | NS | t |
| BS (mg/dL) | 109.18 ± 33.29 | 104.53 ± 23.22 | 17 | 0.165 | NS | t |
| IRI (μU/ml) | 11.25 ± 4.09 | 10.38 ± 4.72 | 17 | 0.358 | NS | t |
| HOMA | 3.13 ± 1.86 | 2.87 ± 2.15 | 17 | 0.231 | NS | t |
| AST (IU/37° C.) | 54.35 ± 29.41 | 35.65 ± 15.68 | 17 | 0.004 | ** | t |
| ALT (IU/37° C.) | 94.88 ± 61.75 | 68.18 ± 57.19 | 17 | 0.002 | ** | t | mean ± SD
* $p < 0.05$,
** $p < 0.01$,
*** $p < 0.001$,
NS not significant
t: paired t-test

| | between two groups | | |
|---|---|---|---|
| | test | P | P |
| BW (kg) | MW | 0.832 | NS |
| T-C (mg/dL) | MW | 0.000 | *** |
| TG (mg/dL) | MW | 0.681 | NS |
| BS (mg/dL) | MW | 0.370 | NS |
| IRI (μU/ml) | MW | 0.378 | NS |
| HOMA | MW | 0.692 | NS |
| AST (IU/37° C.) | MW | 0.042 | * |
| ALT (IU/37° C.) | MW | 0.091 | NS |

MW: Mann-Whitney test

Figure 2:
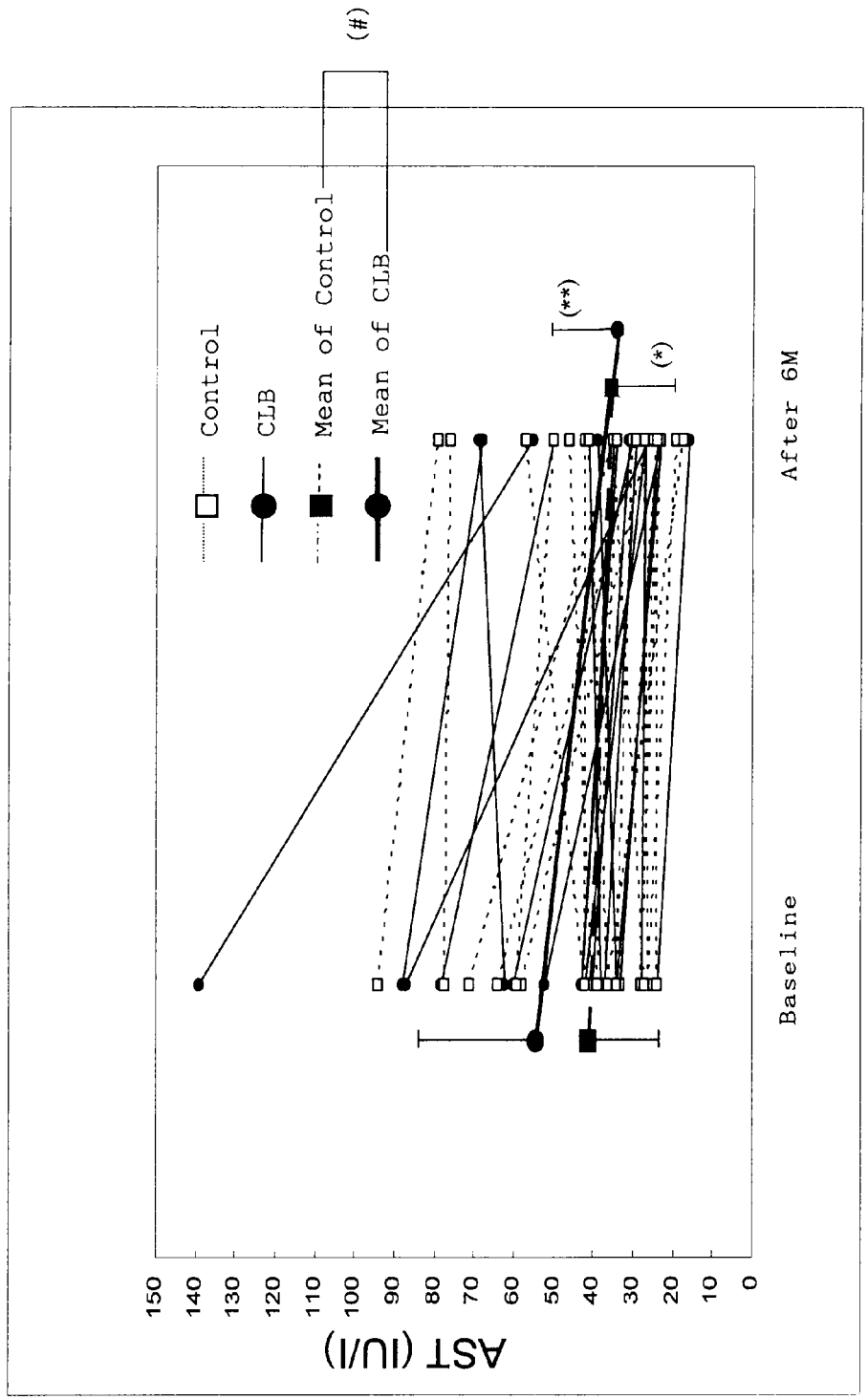
FIG. 2 The figure shows changes in the AST values between before and after the test in the control group and the colestimide administration group.

The control group showed significant effects on the body weight, total cholesterol, triglyceride and AST by comparison between before and after the test. The colestimide administration group showed significant effects on the body weight, total cholesterol, AST and ALT by comparison between before and after the test. A significant difference was found in the total cholesterol and AST between the control group and the colestimide administration group by comparison of changes between before and after the test (FIGS. 1 and 2). In the Figures, CLB shows a colestimide administration group.

(5) Conclusion

In NASH cases having hyperlipidemia or obesity as a complication, the colestimide administration group showed a significant decrease in ALT, which was absent in the control group. In addition, by the intergroup analyses between before and after the test, a significant difference was found in total cholesterol and AST. Accordingly, addition of colestimide to the lifestyle guidance is expected to provide further treatment effects.

Improvement of NASH is based on a liver marker such as ALT and the like or fibrosis as an index (Medical Care Guide of NASH•NAFLD (edited by the Japan Society of Hepatology) BUNKODO, p 40-42, published on Aug. 22, 2006). The decrease in the ALT and AST values in the Examples suggests improvement of NASH.

Example 2

Effect of Colestimide on NASH Patients

Using the same subjects as in Example 1, the effects of colestimide were further studied by addition of measurement items shown in Table 2.

The results of the control group and the colestimide administration group are shown in Table 2.

TABLE 2

|  | Baseline | After 6 months | N | p | Before and after administration test |
|---|---|---|---|---|---|
| Control | | | | | |
| BMI (kg/m$^2$) | 26.68 ± 4.28 | 25.94 ± 4.22 | 21 | ** | t |
| LDL-C (mg/mL) | 148.63 ± 23.11 | 102.71 ± 129.99 | 18 | NS | t |
| HDL-C (mg/mL) | 49.48 ± 14.14 | 81.90 ± 136.63 | 21 | NS | t |
| Visceral fat (cm$^2$) | 186.27 ± 71.48 | 171.20 ± 72.85 | 15 | ** | t |
| HbA1C (%) | 5.69 ± 0.58 | 5.74 ± 0.64 | 17 | NS | t |
| Hyaluronic acid (ng/mL) | 45.75 ± 52.07 | 39.50 ± 41.17 | 16 | NS | w |
| Colestimide | | | | | |
| BMI (kg/m$^2$) | 25.90 ± 3.97 | 25.14 ± 3.33 | 17 | ** | t |
| LDL-C (mg/mL) | 161.04 ± 34.32 | 113.70 ± 29.01 | 16 | *** | t |
| HDL-C (mg/mL) | 50.59 ± 19.32 | 57.71 ± 18.25 | 17 | * | t |
| Visceral fat (cm$^2$) | 155.20 ± 39.38 | 132.27 ± 48.39 | 15 | ** | t |
| HbA1C (%) | 5.59 ± 1.02 | 5.48 ± 0.87 | 17 | * | t |
| Hyaluronic acid (ng/mL) | 46.18 ± 51.29 | 37.41 ± 71.95 | 17 | * | w | mean ± SD
* $p < 0.05$,
** $p < 0.01$,
*** $p < 0.001$,
NS not significant
t: paired t-test
w: Wilcoxon singned-ranks test

|  | between two groups | |
|---|---|---|
|  | test | P |
| BMI (kg/m$^2$) | MW | NS |
| LDL-C (mg/mL) | MW | ** |
| HDL-C (mg/mL) | MW | NS |
| Visceral fat (cm$^2$) | MW | NS |
| HbA1C (%) | MW | NS |
| Hyaluronic acid (ng/mL) | MW | NS |

MW: Mann-Whitney test

The control group showed significant effects in BMI and visceral fat by comparison between before and after the test. The colestimide administration group showed significant effects in BMI, LDL cholesterol, HDL cholesterol, visceral fat, hyaluronic acid and HbAlC by comparison between before and after the test.

In addition, the results of the control group and the colestimide administration group of obesity patients with BMI of not less than 25 are shown in Table 3.

TABLE 3

|  | Baseline | After 6 months | N | p | Before and after administration test |
|---|---|---|---|---|---|
| Control | | | | | |
| Hyaluronic acid (ng/mL) | 21.63 ± 15.11 | 18.75 ± 10.74 | 8 | NS | w |
| Adiponectin (μg/mL) | 5.90 ± 1.39 | 6.22 ± 1.46 | 6 | NS | t |
| Macromolecule adiponectin (μg/mL) | 4.55 ± 6.81 | 2.37 ± 1.01 | 6 | NS | t |
| Colestimide | | | | | |
| Hyaluronic acid (ng/mL) | 38.00 ± 37.69 | 21.71 ± 26.99 | 7 | * | w |
| Adiponectin (μg/mL) | 8.20 ± 5.73 | 10.32 ± 5.37 | 6 | * | t |
| Macromolecule adiponectin (μg/ml) | 3.45 ± 2.76 | 4.55 ± 3.35 | 6 | * | t | mean ± SD
* $p < 0.05$,
** $p < 0.01$,
*** $p < 0.001$,
NS not significant
t: paired t-test
w: Wilcoxon singned-ranks test

|  | between two groups | |
|---|---|---|
|  | test | P |
| Hyaluronic acid (ng/mL) | MW | * |
| Adiponectin (μg/mL) | MW | NS |
| Macromolecule adiponectin (μg/mL) | MW | * |

MW: Mann-Whitney test

The control group did not show significant effect in any item by comparison between before and after the test. The colestimide administration group showed significant effects in all items by comparison between before and after the test. By the intergroup analyses between before and after the test, a significant difference was found in hyaluronic acid and macromolecule adiponectin.

(5) Conclusion

In NASH cases having hyperlipidemia or obesity as a complication, the colestimide administration group showed significant differences in the decrease of LDL-cholesterol, increase of HDL-cholesterol, and decrease of hyaluronic acid (an index of fibrosis), which were not found in the control group. In addition, by the intergroup analyses between before and after the test, a significant difference was found in the decrease of LDL-cholesterol. Furthermore, the obesity patients with BMI of not less than 25, who were administered with colestimide, showed increased adipocytokine (adiponectin, macromolecule adiponectin) values after the test as compared to those before the test. Adipocytokine is a second hit cause in the onset mechanism of NASH, and patients who developed NASH show lower blood concentrations than healthy subjects. Accordingly, a combined use of colestimide administration during treatment is expected to enhance the treatment effects as compared to lifestyle guidance alone.

From the foregoing, colestimide is considered to also act, in addition to hypolipidemic action (first hit cause), on a second hit cause such as adipocytokine and the like, and improve AST, ALT and fibrosis.

Discussion

The action mechanism of colestimide is promotion of catabolism of cholesterol to bile acid in the liver by inhibiting the enterohepatic circulation of bile acid due to promoted adsorption and excretion of bile acid in the gastrointestinal tract. As a result, the cholesterol pool in the liver decreases, which is compensated for by promoted blood LDL uptake by increased liver LDL receptors, thus resulting in decreased serum total cholesterol. It is considered that direct adsorption of exogenous cholesterol and inhibition of cholesterol absorption by inhibition of bile acid micelle formation also contribute to the decrease of serum total cholesterol. Therefore, the action mechanism of colestimide against NASH is considered to act not only on the first hit cause but also the second hit cause such as adipocytokine and the like, and improve AST, ALT and fibrosis.

This application is based on a patent application No. 2007-276510 filed in Japan (filing date: Oct. 24, 2007), the contents of which are incorporated in full herein by this reference.

What is claimed is:

1. A method of treating nonalcoholic steatohepatitis in a patient in need of such treatment, the method comprising administering a therapeutically effective amount of colestimde, as a sole active ingredient, to the patient to treat the nonalcoholic steatohepatitis.

2. The method of claim 1, wherein the administering is oral administration.

3. The method of claim 1, wherein the colestimide is administered in the form of a solid, a tablet, a capsule or a liquid.

4. The method of claim 3, wherein the colestimide is present in an amount of 5 to 95 wt %.

5. The method of claim 3, wherein the colestimide is present in an amount of 25 to 90 wt %.

6. The method of claim 3, wherein the colestimide is present in an amount of 75 to 85 wt %.

7. The method of claim 1, wherein the colestimide is administered in an amount of 1 to 10 g per day.

8. The method of claim 1, wherein the colestimide is administered in an amount of 1.5 to 6 g per day.

9. The method of claim 1, wherein the colestimide is administered in an amount of 3 to 4.5 g per day.

* * * * *